(12) United States Patent
Hansson et al.

(10) Patent No.: US 8,487,074 B2
(45) Date of Patent: Jul. 16, 2013

(54) MODULATION OF LIPID RAFTS

(75) Inventors: Hans-Arne Hansson, Hovas (SE);
Stefan Lange, Goteborg (SE)

(73) Assignee: Lantmannen AS-Faktor AB, Stockholm (SE)

( * ) Notice: Subject to any disclaimer, the term of this patent is extended or adjusted under 35 U.S.C. 154(b) by 1013 days.

(21) Appl. No.: 12/289,390

(22) Filed: Oct. 27, 2008

(65) Prior Publication Data

US 2009/0149382 A1    Jun. 11, 2009

Related U.S. Application Data

(63) Continuation of application No. PCT/SE2007/000415, filed on Apr. 27, 2007.

(60) Provisional application No. 60/920,826, filed on Mar. 30, 2007.

(30) Foreign Application Priority Data

Apr. 27, 2006 (SE) ...................................... 0600933

(51) Int. Cl.
*C07K 14/00* (2006.01)

(52) U.S. Cl.
USPC ........... 530/324; 530/300; 530/326; 530/327; 530/328

(58) Field of Classification Search
USPC .......................... 530/300, 324, 326, 327, 328
See application file for complete search history.

(56) References Cited

U.S. PATENT DOCUMENTS

| | | | |
|---|---|---|---|
| 6,020,143 A * | 2/2000 | St. George-Hyslop et al. | 435/7.1 |
| 2007/0009575 A1 * | 1/2007 | Hansson et al. | 424/439 |

FOREIGN PATENT DOCUMENTS

| | | |
|---|---|---|
| WO | WO 96/17602 A1 | 6/1996 |
| WO | WO 97/08202 A1 | 3/1997 |
| WO | WO 98/21978 A1 | 5/1998 |
| WO | WO 00/38535 A1 | 7/2000 |
| WO | WO 2005/030246 A1 | 4/2005 |
| WO | WO 2007/126363 A2 | 11/2007 |
| WO | WO 2007/126365 A2 | 11/2007 |

OTHER PUBLICATIONS

Clodfelder-Miller (Diabetes 55(12), 3320-3325, 2006).*
Janson Juliette (Diabetes 53(2), 474-481, 2004).*
Abstract of Fricker WO 95/08992, Apr. 1995.*
Rajendran, Lawrence et al; *Raft Association and Lipid Droplet Targeting of Flotillins Are Independent of Caveolin*; Biol. Chem., vol. 388, pp. 307-314; Mar. 2007.
Alvarado, J.A. et al; *A New Insight Into the Cellular Regulation of Aqueous Outflow*; www.bjophthalmol.com, Dec. 13, 2007, XP-002462343, pp. 1500-1505.
Freeman, Michael R. et al; *Transit of Hormonal and EGF Receptor-Dependent Signals Through Cholesterol-Rich Membranes*; www.elsevier.com, Steroids 72 (2007) pp. 210-217.
Márquez, Diana C., et al; *Estrogen Receptiors in Membrane Lipid Rafts and Signal Transduction in Breast Cancer*; Molecular and Cellular Endocrinology 246 (2006) pp. 91-100.
Helms, J. Bernd and Zurzolo, Chiara; *Lipids as Targeting Signals: Lipid Rafts and Intracellular Trafficking*; Traffic 2004, vol. 5, Blackwell Munksgaard, pp. 247-254.
Chini, B and Parenti, M; *G-Protein Coupled Receptors in Lipid Rafts and Caveolae: How, When and Why Do They Go There?*; Journal of Molecular Endocrinology (2004) 32, pp. 325-338.
Triantafilou, Kathy and Triantafilou, Martha; *Lipid-Raft-Dependent Coxsackievirus B4 Internalization and Rapid Targeting to the Golgi*; Virology 326 (2004) pp. 6-19.
Pohl, Jürgen et al; Long-Chain Fatty Acid Uptake Unto Adipocytes Depends on Lipid Raft Function; *Biochemistry* 2004, 43, pp. 4179-4187.
Lange, Stefan and Lönnroth, Ivar; *The Antisecretory Factor: Synthesis, Anatomical and Cellular Distribution, and Biological Action in Experimental and Clinical Studies*; International Review of Cytology, vol. 210, pp. 39-75, (2001).
Dermine, Jean-François et al; *Flotillin-1-Enriched Lipid Raft Domains Accumulate on Maturing Phagosomes*; The Journal of Biological Chemistry, vol. 276, No. 21, May 25, 2001, pp. 18507-18512.
Kurzchalia, Teymuras V. and Parton, Robert G.; *Membrane Microdomains and Caveolae*; Current Opinion in Cell Biology, 1999, pp. 424-431.

* cited by examiner

*Primary Examiner* — David Lukton
(74) *Attorney, Agent, or Firm* — Womble Carlyle Sandridge & Rice LLP

(57) ABSTRACT

The present invention relates to the use of an antisecretory protein, derivative, homologue, and/or fragment thereof, having equivalent activity, and/or a pharmaceutically active salt thereof, for the manufacture of a pharmaceutical composition and/or a medical food for the treatment and/or prevention of dysfunction, e.g. abnormal function, hypo- or hyper-function of lipid rafts, receptors and/or caveolae. A dysfunction of lipid rafts, receptors and/or caveolae may be caused by or be a cause of a variety of other conditions, which are also encompassed by the present invention, such as vascular, and lung dysfunctions, and/or endocrine disorders, e.g. diabetes and related disorders. Furthermore, the invention relates to a method for the treatment and/or prevention of dysfunction of lipid rafts and/or caveolae in a mammal in need thereof.

10 Claims, 1 Drawing Sheet

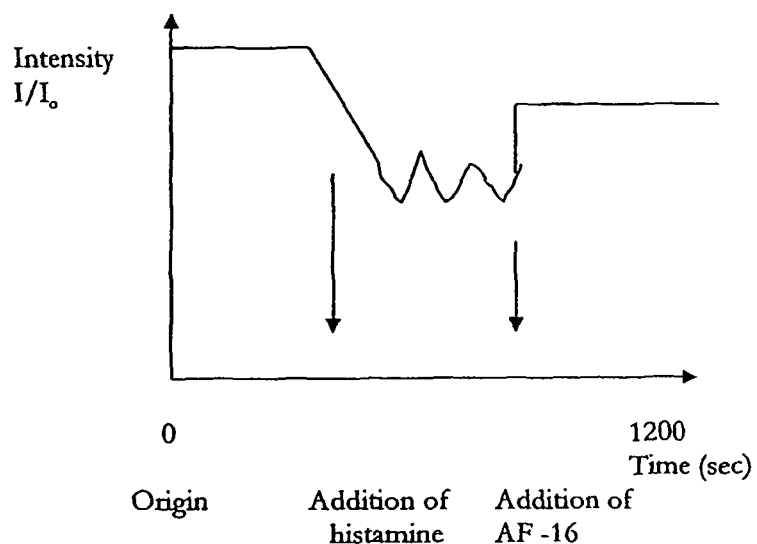

SEQUENCE LISTING

```
<160> NUMBER OF SEQ ID NOS: 12

<210> SEQ ID NO 1
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 1

Val Cys His Ser Lys Thr Arg Ser Asn Pro Glu Asn Asn Val Gly Leu
1               5                   10                  15

<210> SEQ ID NO 2
<211> LENGTH: 8
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 2

Ile Val Cys His Ser Lys Thr Arg
1               5

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 3

Val Cys His Ser Lys Thr Arg
1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 4

Cys His Ser Lys Thr Arg
1               5

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 5

His Ser Lys Thr Arg
1               5

<210> SEQ ID NO 6
<211> LENGTH: 382
<212> TYPE: PRT
<213> ORGANISM: Homo sapiens

<400> SEQUENCE: 6

Met Val Leu Glu Ser Thr Met Val Cys Val Asp Asn Ser Glu Tyr Met
1               5                   10                  15

Arg Asn Gly Asp Phe Leu Pro Thr Arg Leu Gln Ala Gln Gln Asp Ala
                20                  25                  30

Val Asn Ile Val Cys His Ser Lys Thr Arg Ser Asn Pro Glu Asn Asn
            35                  40                  45

Val Gly Leu Ile Thr Leu Ala Asn Asp Cys Glu Val Leu Thr Thr Leu
```

```
                50                  55                  60
Thr Pro Asp Thr Gly Arg Ile Leu Ser Lys Leu His Thr Val Gln Pro
 65                  70                  75                  80

Lys Gly Lys Ile Thr Phe Cys Thr Gly Ile Arg Val Ala His Leu Ala
                 85                  90                  95

Leu Lys His Arg Gln Gly Lys Asn His Lys Met Arg Ile Ile Ala Phe
            100                 105                 110

Val Gly Ser Pro Val Glu Asp Asn Glu Lys Asp Leu Val Lys Leu Ala
            115                 120                 125

Lys Arg Leu Lys Lys Glu Lys Val Asn Val Asp Ile Ile Asn Phe Gly
        130                 135                 140

Glu Glu Glu Val Asn Thr Glu Lys Leu Thr Ala Phe Val Asn Thr Leu
145                 150                 155                 160

Asn Gly Lys Asp Gly Thr Gly Ser His Leu Val Thr Val Pro Pro Gly
                165                 170                 175

Pro Ser Leu Ala Asp Ala Leu Ile Ser Ser Pro Ile Leu Ala Gly Glu
            180                 185                 190

Gly Gly Ala Met Leu Gly Leu Gly Ala Ser Asp Phe Glu Phe Gly Val
        195                 200                 205

Asp Pro Ser Ala Asp Pro Glu Leu Ala Leu Ala Leu Arg Val Ser Met
210                 215                 220

Glu Glu Gln Arg His Ala Gly Gly Gly Ala Arg Ala Ala Arg Ala
225                 230                 235                 240

Ser Ala Ala Glu Ala Gly Ile Ala Thr Thr Gly Thr Glu Asp Ser Asp
                245                 250                 255

Asp Ala Leu Leu Lys Met Thr Ile Ser Gln Gln Glu Phe Gly Arg Thr
            260                 265                 270

Gly Leu Pro Asp Leu Ser Ser Met Thr Glu Glu Gln Ile Ala Tyr
        275                 280                 285

Ala Met Gln Met Ser Leu Gln Gly Ala Glu Phe Gly Asn Ala Glu Ser
            290                 295                 300

Ala Asp Ile Asp Ala Ser Ser Ala Met Asp Thr Ser Glu Pro Ala Lys
305                 310                 315                 320

Glu Glu Asp Asp Tyr Asp Val Met Gln Asp Pro Glu Phe Leu Gln Ser
                325                 330                 335

Val Leu Glu Asn Leu Pro Gly Val Asp Pro Asn Glu Ala Ile Arg
            340                 345                 350

Asn Ala Met Gly Ser Leu Pro Pro Arg Pro Pro Arg Thr Ala Arg Arg
        355                 360                 365

Thr Arg Arg Arg Lys Thr Arg Ser Glu Thr Gly Gly Lys Gly
370                 375                 380

<210> SEQ ID NO 7
<211> LENGTH: 163
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(34)
<223> OTHER INFORMATION: This region may or may not be present
<220> FEATURE:
<221> NAME/KEY: MOD_RES
<222> LOCATION: (35)..(35)
<223> OTHER INFORMATION: May not be present
<220> FEATURE:
<221> NAME/KEY: MOD_RES
```

```
<222> LOCATION: (38)..(38)
<223> OTHER INFORMATION: His, Arg or Lys
<220> FEATURE:
<221> NAME/KEY: MOD_RES
<222> LOCATION: (39)..(39)
<223> OTHER INFORMATION: Ser or Leu
<220> FEATURE:
<221> NAME/KEY: MOD_RES
<222> LOCATION: (41)..(41)
<223> OTHER INFORMATION: Thr or Ala
<220> FEATURE:
<221> NAME/KEY: MOD_RES
<222> LOCATION: (43)..(163)
<223> OTHER INFORMATION: This region, or portions thereof, may or may
      not be present; see specification as filed for detailed
      description

<400> SEQUENCE: 7

Met Val Leu Glu Ser Thr Met Val Cys Val Asp Asn Ser Glu Tyr Met
1               5                   10                  15

Arg Asn Gly Asp Phe Leu Pro Thr Arg Leu Gln Ala Gln Gln Asp Ala
            20                  25                  30

Val Asn Ile Val Cys Xaa Xaa Lys Xaa Arg Ser Asn Pro Glu Asn Asn
        35                  40                  45

Val Gly Leu Ile Thr Leu Ala Asn Asp Cys Glu Val Leu Thr Thr Leu
    50                  55                  60

Thr Pro Asp Thr Gly Arg Ile Leu Ser Lys Leu His Thr Val Gln Pro
65                  70                  75                  80

Lys Gly Lys Ile Thr Phe Cys Thr Gly Ile Arg Val Ala His Leu Ala
                85                  90                  95

Leu Lys His Arg Gln Gly Lys Asn His Lys Met Arg Ile Ile Ala Phe
            100                 105                 110

Val Gly Ser Pro Val Glu Asp Asn Glu Lys Asp Leu Val Lys Leu Ala
        115                 120                 125

Lys Arg Leu Lys Lys Glu Lys Val Asn Val Asp Ile Ile Asn Phe Gly
    130                 135                 140

Glu Glu Glu Val Asn Thr Glu Lys Leu Thr Ala Phe Val Asn Thr Leu
145                 150                 155                 160

Asn Gly Lys

<210> SEQ ID NO 8
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Val Cys His Ser Lys Thr Arg Ser Asn Pro Glu Asn Asn Val Gly Leu
1               5                   10                  15

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ile Val Cys His Ser Lys Thr Arg
1               5
```

```
<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Val Cys His Ser Lys Thr Arg
1               5

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Cys His Ser Lys Thr Arg
1               5

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

His Ser Lys Thr Arg
1               5
```

MODULATION OF LIPID RAFTS

CROSS-REFERENCE TO RELATED APPLICATION

This application is a Continuation of International Application PCT/SE2007/000415, filed Apr. 27, 2007, which claims the benefit of Swedish Patent Application No. 0600933-6 filed Apr. 27, 2006, and U.S. Provisional Application No. 60/920,826 filed Mar. 30, 2007. The entire specification claims and drawings of the applications listed above are incorporated herewith by reference for all purposes.

FIELD OF INVENTION

The present invention relates to the use of antisecretory proteins, derivatives, homologues, and/or fragments thereof, having equivalent functional activity, and/or a pharmaceutically active salt thereof, for the manufacture of a pharmaceutical composition for the treatment and/or prevention of structural disorganization and dysfunction of lipid rafts and/or caveolae in cell membranes, as well as binding proteins, receptors, neurotransmitters, ion channels, water channels, cytoskeleton and G-protein systems related to lipid rafts and caveolae, including uptake and release of compounds. The pharmaceutical composition is herein used to monitor and/or beneficially affect the structure, distribution and multiple functions of lipid rafts, receptors and/or caveolae in membranes. Examples of such beneficial affecting can be to counteract abnormal function, such as hypo- or hyper-function, to restore and/or normalize the lipid rafts, receptors and/or caveolae structurally and functionally, to improve survival and/or rescue at diseases, injuries, repair processes and other dysfunctions. Additionally, the invention relates to the use of said pharmaceutical composition for monitoring intracellular transport and release of cell products, as well as for normalizing the distribution of tissue constituents.

BACKGROUND OF THE INVENTION

Lipid rafts are dynamic, heterogeneous micro domains forming specialized regions in cell membranes, and are enriched in cholesterol and glycolipids, most evidently sphingolipids such as GMI (Ross & Pawlina, 2006; Pollard & Earnshaw, 2002). One definition of them in vitro is as remaining insoluble after extraction with the detergent Triton X-100, used diluted and in the cold. Such a detergent resistant membrane fraction is recovered as a low-density band isolated by flotation gradients. The prevalence of lipid rafts is reduced by depletion or disorganization of cholesterol in cell membranes. Lipid rafts are in close relation to and connected to the cytoskeleton, and involved in cell polarization. They constitute specialized micro domains, prevalent in membranes in cells and tissues at all ages e.g. in embryos, fetuses as well as in young, adult and old individuals.

Proteins of key importance for cohesion and signal transduction are enriched in the lipid rafts, such as receptors, cell attachment proteins, ion transporters, and ion channel complexes including e.g. aquaporines, as well as chemokine receptors, neurotransmitter receptors, hormone receptors and growth factor receptors. These proteins and protein complexes are interacting with the intracellular G protein systems, which transfer the message received by e.g. the receptors to the cell's cytoplasm and nucleus (Dermine et al., 2001; Ross & Pawlina, 2006; Pollard & Earnshaw, 2002; Helms & Zurzolo, 2004; Chini & Parenti, 2004; Head et al., 2006; Mahmutefendic et al., 2007). The distribution and concentrations of the key ion in monitoring cellular activity, $Ca^{2+}$, has been demonstrated to be closely related to lipid rafts and to caveolae. Additional proteins, such as connexins, CD38, CD19, Thy-1 and CD59, are anchored to lipid rafts, commonly via glycosylphosphatidylinositol (GPI) anchored proteins and receptors, which enables them to interact with cell functions. Sphingolipids, as illustrated by the ganglioside GMI, the target for cholera toxin, are enriched in and characterizing lipid rafts. In addition, neurotransmitter receptors and other constituents of synapses and neuronal processes as well as growth factor receptors are among the wide range of proteins prevalent in the lipid rafts e.g. in such highly specialized cells as neurons. Calcium ion channels and transporters, of key importance in regulating cell functions and interactions, are to a large extent confined to lipid rafts (A Spat, 2007). This may be illustrated by the observation that disruption of lipid rafts hampers or even prevents a cell's ability to propagate traveling $Ca^{2+}$ waves in cells. Further, calcium ion bursts significantly influence key functions in normal cells and in pathologically altered cells, e.g. cell division, cell survival and cell death.

Further, lipid rafts are considered to play a key role in intracellular protein trafficking, receptor and lipid dynamics. Messages and actions by all these receiving and conveying proteins are transmitted to the interior of cells via G-linked protein systems, via enzyme systems or with the aid of the cytoskeleton (Triantafilou & Triantafilou, 2004). The physical state of lipid rafts is e.g. known to be conducive to concentrate and constrain the mobility of multiple proteins to facilitate the dynamic assembly of competent signaling complexes.

What is more, lipid rafts are considered to have the capacity to regulate activation, signaling and rearrangement of the cytoskeleton, which renders them critically important to the mechanisms governing cellular locomotion including directional migration, as well as for maintaining the shape and size of cells and associated transport. The cytoskeleton is further of key importance for intracellular trafficking of cell constituents and for sensing dynamic and static load on cells.

Lipid rafts are thus dynamic structures, usually with a diameter in the order of 5-50 nm, with a considerable range of variation. There are a multitude of approaches to demonstrate the presence of lipid rafts, e.g. by immunohistochemical and immunochemical demonstration of GMi which has a very high affinity to cholera toxin. Another way to demonstrate their presence and position is to isolate cell membranes after having disrupted the cells and then isolated a detergent resistant fraction at a defined temperature, as described in commonly available cell biology textbooks.

Flotillin, caveolin and reggie may be used to immunohistochemically identify lipid rafts. Of those proteins, flotillin may further associate with lipid droplets. Atomic force microscopy and related approaches add to the techniques enabling the visualization of lipid rafts. Exposure of cells to cyclodextrine and variants thereof, causing a depletion of cholesterol from the membranes, constitutes an alternative way of demonstrating the prevalence of lipid rafts.

Caveolae constitute a specialized type of lipid raft. They are dynamic structures characterized by focal enrichment in membranes of cholesterol and sphingolipids, transducing signals between the environment and the interior of cells as well as connecting to the cytoskeleton. In contrast to other lipid rafts, caveolae are larger and usually appearing as flask-shaped pits or invaginations in the cell membranes and as vesicles (Kurzchalia & Parton, 1999). Their size is commonly in the order of 0.1 pm, but with considerable variations.

Caveolae are prevalent in e.g. cardiac and smooth muscle cells, endothelial cells, macrophages, and adipocytes, i.e. in virtually all-mammalian cells although in a highly varying frequency.

Lipid rafts and caveolae have been disclosed to harbor and influence NO (nitrogen oxide) generating system. In addition to conveying signals to and from a cell, caveolae are involved in the trafficking of fluid and various compounds to and from a cell, endocytosis and the regulation, trafficking, efflux and maintenance of fatty acids and cholesterol in cells and their environment (Pohl et al., 2004; Rajendran et al., 2007). Caveolae constituents and lipid rafts are further involved in the processing of 13 amyloid precursor protein ((3APP) and amyloid p (A(3), proteins related to preferentially Alzheimer's diseases but also to other neurodegenerative disorders and neurotrauma (Graham & Lantos, 2002).

Tumor cells are known to have lipid rafts and as well caveolae. Thus, it is e.g. possible to impair the growth and migration of tumor cells by disrupting or to a variable extent disintegrating these structures (Marquez, D C et al., 2006; Freeman et al., 2007).

The importance of lipid rafts and caveolae has been further elucidated in genetically modified animals. Knockout mice deficient in caveolin develop dilated cardiomyopathy and pulmonary hypertension (Mathew et al., 2004). Further, lipid rafts and caveolae are related to insulin stimulated transporter systems such as steroid hormone conveying systems.

It is concluded that lipid rafts and caveolae, constituting highly dynamic structures, closely related but in some aspects also diverging, are prevalent in mammalian cells and exert a multitude of important functions. Approaches available at present enable the disruption or depletion of lipid rafts and caveolae, but there is no known way to restore and/or normalize the structure, distribution, frequency and/or function of lipid rafts and signaling and mass transfer proteins, organized in the lipid raft.

The antisecretory protein is a 41 kDa protein that originally was described to provide protection against diarrhoeal diseases and intestinal inflammation (for a review, see Lange and Lonnroth, 2001). The antisecretory protein has been sequenced and its cDNA cloned. The equivalent activity seems to be mainly exerted by a peptide located between the positions 35 and 50 of the antisecretory protein sequence. Immunochemical and immunohistochemical investigations have revealed that the antisecretory protein is present in and may also be synthesized by most tissues and organs in a body. Synthetic peptides, comprising the antidiarrhoeic sequence, have been characterized (WO 97/08202; WO 05/030246). Antisecretory factors have previously been disclosed to normalize pathological fluid transport and/or inflammatory reactions, such as in the intestine and the choroid plexus in the central nervous system after challenge with the cholera toxin (WO 97/08202). Use of natural antisecretory factors to food and feed was therefore suggested to be useful for the treatment of edema, diarrhea, dehydration and inflammation in WO 97/08202. WO 98/21978 discloses the use of products having enzymatic activity for the production of a food that induces the formation of antisecretory proteins. WO 00/038535 further discloses the food products enriched in antisecretory proteins as such.

Antisecretory protein and fragments thereof have also been shown to improve the repair of nervous tissue, and the proliferation, apoptosis, differentiation, and/or migration of stem and progenitor cells and cells derived thereof in the treatment of conditions associated with loss and/or gain of cells (WO 05/030246).

Antisecretory factors (AF), specifically proteins and peptides, as described in detail in WO 97/08202, are effective in abolishing hypersecretory conditions and diseases in the intestine, such as diarrhea. Other examples related to effects of AF in relation to hypersecretory conditions are e.g. inflammatory bowel diseases, brain edema, glaucoma, elevated intracranial pressure, Morbus Méniére, and mastitis. AF has as well been considered for the treatment of glaucoma (WO 97/08202).

It has recently been recognized that the structure, prevalence, distribution and function of lipid rafts, which have been altered due to abnormal cell function, excessive or abnormal load, infection, or by a toxic compound or a drug may be monitored and even normalized with the aid of certain specific proteins and related compounds.

Astonishingly enough, the inventors have now been able to prove that the protein Antisecretory Factor (AF) and peptides derived thereof, e.g. AF-16 and AF-8, can affect the structure, prevalence, distribution and/or function of lipid rafts, receptors and/or caveolae, which have been altered due to abnormal cell function, excessive or abnormal load, infection, or by a toxic compound and/or a drug in cells, tissues and/or organs, in such a way that it is for the first time possible to monitor, control and/or even normalize the functions confined to or related to lipid rafts and/or caveolae.

SUMMARY OF THE PRESENT INVENTION

The present invention relates to the use of a pharmaceutical composition comprising an antisecretory protein, a homologue, derivative, and/or fragment thereof, having antisecretory and/or equivalent functional and/or analogue activity, or a pharmaceutically active salt thereof, for the manufacture of a pharmaceutical composition for the treatment and/or prevention of dysfunction of lipid rafts, receptors and/or caveolae in cell membranes, such as abnormal, insufficient, hypo- and/or hyper-function.

The invention also relates to the use of a pharmaceutical composition comprising an antisecretory protein, a homologue, derivative, and/or fragment thereof, having equivalent and/or analogue activity, or a pharmaceutically active salt thereof, for the manufacture of a pharmaceutical composition for the treatment and/or prevention of various conditions associated with dysfunction of lipid rafts, receptors and/or caveolae, such as any condition selected from the group consisting of vascular dysfunction, cardiovascular dysfunction, lung dysfunction, hyperplasia and/or hypertrophy of cells and tissue, cardiovascular dysfunction, cardiomyopathy and pulmonary hypertension, formation of scar tissue, reactive formation of excessive tissue, and diabetes mellitus, such as diabetes type I and/or II.

Furthermore, the invention relates to the use of a pharmaceutical composition comprising an antisecretory protein, a homologue, derivative, and/or fragment thereof, having equivalent activity, or a pharmaceutically active salt thereof, for the manufacture of a pharmaceutical composition for the treatment and/or prevention of various conditions associated with dysfunction of lipid rafts and/or caveolae, wherein said pharmaceutical composition will beneficially affect e.g. transfer of constituents across cellular barriers, repair of tissues and organs, reactive formation of excessive tissue and/or repair and regeneration of epithelial cell covering.

In another aspect, the present invention relates to the use of a pharmaceutical composition comprising an antisecretory protein, a homologue, derivative, and/or fragment thereof, having equivalent functional activity, or a pharmaceutically active salt thereof, for the manufacture of a pharmaceutical composition for the treatment and/or prevention of various conditions associated with dysfunction of lipid rafts and/or caveolae, being selected from the group consisting of Alzheimer's diseases, any other neurodegenerative disorders and neurotrauma.

In a preferred embodiment, said antisecretory protein consists of a sequence according to the following formula

X1-V-C-X2-X3-K-X4-R-X5,    (SEQ ID NO: 7)

wherein X1 is I, amino acids 1-35 of SEQ ID NO: 6, or is absent, X2 is H, R or K, X3 is S or L, X4 is T or A, X5 is amino acids 43-46, 43-51, 43-80 or 43-163 of SEQ ID NO: 6, or is absent. Furthermore, the invention relates to a method for the treatment and/or prevention of a medical condition associated with dysfunction in lipid rafts, receptors and/or caveolae, such as mentioned in the above, said method comprising administering to a mammal in need thereof an therapeutically effective amount of a pharmaceutical composition comprising an antisecretory protein, a derivative, homologue, and/or fragment thereof, having equivalent activity, and/or a pharmaceutically active salt thereof.

The invention is also related to various administration doses and routes suitable for the intended purpose of treatment as well as the patient's age, gender, condition etc.

Furthermore, said pharmaceutical composition can of course comprise two or more antisecretory proteins, as well as further comprising a pharmaceutically acceptable excipient. The pharmaceutical composition is herein formulated for intraocular, intranasal, oral, local, subcutaneous and/or systemic administration and can e.g. be formulated for administration as a spray, aerosol, and inhaler or by a nebulizer. When formulated for administration systemically to the blood said composition is preferably formulated at a dose of 0.1 µg to 10 mg per application and kg body weight and day, such as at a dose of 0.1 µg to 1 mg per application and kg body weight and day, preferably again at 1-500 µg per application and kg body weight and day, such as at 1-50 µg per application and kg body weight and day. Such an administration can be performed either as a single dose or as multiple daily applications.

In general, the present invention relates to the use of an antisecretory protein, a homologue, derivative, and/or fragment thereof, having equivalent activity, or a pharmaceutically active salt thereof, for the manufacture of a pharmaceutical composition for the treatment and/or prevention of various conditions associated with dysfunction of lipid rafts and/or caveolae. In a preferred embodiment, said composition can be employed to monitor and normalize the structure, distribution and function of caveolae and of lipid rafts, i.e. of specialized micro domains, e.g. to restore them structurally and functionally, to improve survival and rescue at diseases, injuries, repair processes and other malfunctions. Additionally, the invention enables monitoring the intracellular transport and release of cell products as well as to normalize the distribution of tissue constituents at various diseases, and/or to monitor the formation of reactive cells and tissues, as well as to reduce the formation of scar tissue including abnormal tissue and organ connections. Further, said composition can also be used to enable treatment of effects exerted by toxic substances and to monitor their long-term effects. In a preferred embodiment, such a condition is selected from the group consisting of trauma, intoxication, infection, malformation, degeneration and another malfunctions or diseases of cells, tissues and organs in a mammalian body.

Without wishing to limit the scope of the present invention to a specific theory, it is postulated that the composition of the present invention comprising an antisecretory protein, a derivative, homologue, and/or fragment thereof, having equivalent activity, and/or a pharmaceutically active salt thereof could exert it's effects through it's beneficial influences on the normalization of structure, distribution and/or function of caveolae and/or lipid rafts in cell membranes.

BRIEF DESCRIPTION OF THE DRAWINGS

FIG. 1: shows a difference in potential over cell membrane in cells with a defective GABA receptor. Histamine or AF-16 is added and the effect of these compounds is measured on the potential of the cell membrane measured in I/lo.

DEFINITIONS AND ABBREVIATIONS

Abbreviations

BP: blood pressure; CSF: cerebrospinal fluid; CNS: central nervous system, i.e. the brain and the spinal cord; IFP: interstitial fluid pressure; PH: pulmonary hypertension; PBS: phosphate buffered saline; AF: antisecretory factor, AF-16: a peptide composed of the amino acids VCHSKTRSNPENNVGL (SEQ ID NO: 8); octa peptide IVCHSKTR (SEQ ID NO: 9); septa peptide VCHSKTR (SEQ ID NO: 10); hexa peptide CHSKTR (SEQ ID NO: 11); penta peptide HSKTR (SEQ ID NO: 12).

Definitions

Proteins are biological macromolecules constituted by amino acid residues linked together by peptide bonds. Proteins, as linear polymers of amino acids, are also called polypeptides. Typically, proteins have 50-800 amino acid residues and hence have molecular weights in the range of from about 6,000 to about several hundred thousand Dalton or more. Small proteins are called peptides or oligopeptides. The terms "protein" and "peptide" may be used interchangeably in the present context.

A "pharmaceutical composition", in the present context, refers to a composition comprising a therapeutically active amount of an antisecretory protein, optionally in combination with a pharmaceutically active excipient, such as a carrier or a vehicle. Said pharmaceutical composition is formulated for the appropriate route of administration, which may vary depending on the condition of the patient, as well as on other factors, such as age or preferred choice. A pharmaceutical composition comprising an antisecretory protein serves as a drug delivery system. The pharmaceutical composition upon administration presents the active substance to the body of a human or an animal. Said pharmaceutical composition may be in the form of e.g. tablets, pills, lozenges, capsules, stool pills, gels, solutions, etc, but is not limited thereto.

The term "pharmaceutically active salt", refers to a salt of an antisecretory protein, which may be any salt derived there from, based on so-called Hofmeiser's series. Other examples of pharmaceutically active salts comprise triflouroacetate, acetate and lysine chloride, but the invention is not limited thereto.

The term "antisecretory" refers in the present context to inhibiting or decreasing secretion, especially intestinal secretions. Hence, the term "antisecretory protein" refers to a protein capable of inhibiting or decreasing secretion in a body.

A "medical food", in the present context, refers to a food, which has been prepared with a composition with an antisecretory protein. Said food may be any suitable food, in fluid or solid form, such as a liquid or a powder, or any other suitable foodstuff. Examples of such matter may be found in WO 0038535. Said constituent may as well induce the uptake, formation and release of an antisecretory protein.

In the present context, an "antisecretory protein", or a homologue, derivative or fragment thereof, may be used interchangeably with the term "antisecretory factors" or "antisecretory factor proteins" as defined in patent WO 97/08202, and refers to an antisecretory protein or a peptide or a homologue, derivative and/or fragment thereof having antisecretory and/or equivalent functional and/or analogue activity. Hence, it is to be understood that an "antisecretory factor, "antisecretory factor protein", "antisecretory peptide", "antisecretory fragment", or an "antisecretory protein" in the present context, also can refer to a derivative, homologue or fragment thereof. These terms may all be used interchangeably in the context of the present invention. Furthermore, in the present context, the term "antisecretory factor" may be abbreviated "AF". Antisecretory protein in the present context also refers to a protein with antisecretory properties as previously defined in WO 97/08202 and WO 00/38535.

Antisecretory factors have also been disclosed e.g. in WO 05/030246. Also intended by the term antisecretory factor is egg yolk enriched in antisecretory factors as disclosed in SE 900028-2 and WO 00/38535 as further described below.

A "nebulizer", in the present context, refers to a medical device that delivers liquid medication in the form of a mist to the airways. "Nebulizer" compressors force air through tubing into a medicine cup filled with liquid medicine. The force of the air breaks the liquid into tiny mist-like particles that can be inhaled deeply into the airways.

The term "aerosol" in the present context refers to a gaseous suspension of fine solid or liquid particles.

DETAILED DESCRIPTION OF THE INVENTION

There is a need for new drugs aimed at pharmacological treatment of medical conditions associated with the dysfunction of lipid rafts and/or caveolae, as presently no adequate therapy is available. The antisecretory proteins have beneficial effects, as exemplified in the following text.

The present invention relates to the monitoring and regulation of the structure and function of lipid rafts and the related structure caveolae, prevalent in cell membranes. Lipid rafts are defined as membrane micro domains, enriched in cholesterol, and in which proteins of importance for e.g. sphingolipids such as GMi transport of ions, cell attachment, growth, signaling and attachment to the cytoskeleton are confined. Caveolae are vesicular or flask-shaped structures, abundant in cells e.g. of the cardiopulmonary and vascular systems, including endothelial cells, smooth muscle cells, epithelial cells, fibroblasts, and cardiac myocytes (Chan and Ye, 2007; Petersen et al., 2007), formed by one or more clusters of lipid raft constituents. Additional proteins associated either alone or in combinations are flotillin, caveolin, and reggie; several variants exist of each one.

Caveolae are prevalent in e.g. cardiac and smooth muscle cells, endothelial cells, macrophages, and adipocytes, they are a specialized type of lipid rafts, being dynamic structures characterized by focal enrichment in membranes of cholesterol and sphingolipids, transducing signals between the environment and the interior of cells as well as connecting to the cytoskeleton. In contrast to other lipid rafts, caveolae are larger and usually appear as flask-shaped pits or invaginations in the cell membranes and as vesicles. Their size is commonly in the order of 0.1 μm, but with considerable variations.

Further, glycophosphatidylinositol-linked proteins and variants thereof constitute anchor proteins attached to and interacting with said structures. Enzymes mediating vascular functions have as well been revealed to be localized to named structures. These dynamic membrane constituents are linked to the interior of a cell via G-protein systems and enzyme systems as well as via the cytoskeleton, thereby enabling these structures to influence and regulate cell functions. Thus, lipid rafts and caveolae have been revealed to be of key importance for the structure and the function of cells. There is no known approach enabling monitoring stabilization and normalization of such membrane structures including the signaling and mass transfer proteins.

The present invention relates to the use of a pharmaceutical composition comprising an antisecretory protein, a homologue, derivative, and/or fragment thereof, having equivalent activity, or a pharmaceutically active salt thereof, for the manufacture of a pharmaceutical composition and/or medical food for the treatment and/or prevention of dysfunction of lipid rafts and caveolae in cell membranes. The invention also relates to the treatment and/or prevention of various conditions associated with dysfunction of lipid rafts and caveolae, such as transfer of constituents across cellular barriers, repair of tissues and organs, hyperplasia and/or hypertrophy of cells and tissue, cardiovascular function, formation of scar tissue, reactive formation of excessive tissue and repair and regeneration of epithelial cell covering.

Furthermore, the invention relates to a method for the treatment and/or normalization of dysfunctions of lipid rafts and caveolae, as mentioned above, said method comprising administering to a mammal in need thereof an therapeutically effective amount of a pharmaceutical composition and/or a medical food comprising an antisecretory protein or a derivative, homologue, fragment or thereof, having equivalent activity, or a pharmaceutically active salt thereof.

The invention is also related to various administration doses and routes suitable for the intended purpose of treatment as well as the patient's age, gender, condition etc.

The treatment according to the invention is likely to be most useful to patients at risk for developing or suffering from dysfunction of lipid rafts and caveolae, or from the uptake or release of pathogenic substances. In addition such treatment is beneficial also in other conditions characterized by abnormal turn over of cells and extracellular matrix constituents.

The presently found proof that antisecretory proteins and peptides are likely to exerted effects on the lipid rafts in cell membranes is indeed astonishing to the person skilled in the art. There are a large number of domains with an average size of much less than a pm, named lipid rafts, characterized by high concentrations of cholesterol and sphingomyelin. The lipid rafts contain a variety of integral and peripheral membrane proteins involved in mass transfer and cell signaling. Such signaling platforms float in the membrane and are equipped with necessary elements for proper function as receptors, coupling factors, effectors enzymes and compounds, and substrates, thereby being able to receive and convey specific ions, molecules and signals. These domains further interact with e.g. the cytoskeleton, and additionally, influence the composition and turn over of the interstitial fluid as well as its pressure. Further, lipid rafts are related to the turn over of caveolae and to the release and internalization of e.g. viruses. There is a clustering in the cell membranes of growth factor receptors, inflammatory signal receptors, ion channels and transporters to the lipid rafts, which undergo dynamic changes related to the prevailing function at each moment.

The use of antisecretory proteins and peptides (AF) is not limited to the tissues, organs and anatomical structures described in the examples, but includes additional symptoms and diseases characterized by dysfunction, abnormal function, hypo- or hyper function of lipid rafts and/or caveolae.

The antisecretory proteins, peptides, derivates and homologues have the capacity to monitor and even normalize the functions of lipid rafts and proteins involved in mass transfer and signaling. The very wide range of effective dose regimes utilized indicates that the risks for side effects and unexpected complications are minimal. Thus, the used approach to monitor and control structures and functions related to lipid rafts and caveolae enables the treatment of excessive loads on cells and tissues as wells as treatment of a patient with a wide range of doses suited to the individual response and the severity of the illness and/or the discomfort.

The pharmaceutical composition according to the present invention can in one context be administrated by application topically, locally in situ, orally, in the nose, subcutaneously and/or systemically via blood vessels or via the respiratory tract.

The antisecretory factor is a class of proteins that occur naturally in the body. The human antisecretory factor protein is a 41 kDa protein, comprising 382 amino acids when isolated from the pituitary gland. The active site with regard to the beneficial effect on lipid raft normalization and or monitoring of caveolae according to the present invention can to be localized to the protein in a region close to the N-terminal of the protein, localized to amino acids 1-163 of SEQ ID NO 6, or to a fragment of this region.

The present inventors have shown that the antisecretory factor is to some extent homologous with the protein S5a, also named Rpn 10, which constitute a subunit of a constituent prevailing in all cells, the 26 S proteasome, more specifically in the 19 S/PA 700 cap. In the present invention, antisecretory proteins are defined as a class of homologus proteins having the same functional properties. The proteasomes have a multitude of functions related to the degradation of surplus proteins as well as short-lived unwanted, denatured, misfolded and otherwise abnormal proteins. Further, the antisecretory factor/S5a/Rpn10 is involved in the distribution and transportation of cell constituents, most evidently proteins.

Homologues, derivatives and fragments of antisecretory proteins and/or peptides according to the present invention all have analogous biological activity of being able to be used for the manufacture of a medicament for the treatment and/or prevention of dysfunctions in lipid rafts and/or caveolae, as well as in a method for treating conditions associated to dysfunctions in lipid rafts and/or caveolae. Homologues, derivatives and fragments, in the present context, comprise at least 4 amino acids of a naturally occurring antisecretory protein, which may be further modified by changing one or more amino acids in order to optimize the antisecretory factor's biological activity in the treatment and/or prevention of conditions related to the present invention. A fragment of an antisecretory protein will generally comprise the peptide/amino acid sequence or a fragment thereof in a preparation in which more than 90%, e.g. 95%, 96%, 97%, 98% or 99% of the protein in the preparation is a protein, peptide and/or fragments thereof of the invention.

Furthermore, any amino acid sequence being at least 70% identical, such as being at least 72%, 75%, 77%, 80%, 82%, 85%, 87%, 90%, 91%, 92%, 93%, 94%, 95%, 96%, 97%, 98%, or 99% identical with the amino acid sequence of an antisecretory protein, peptide, homologue, derivative and/or fragment according to the invention, is also considered to be inside the scope of the present invention. In the present context the terms homologous and identity are used interchangeably, i.e. an amino acid sequence having a specified degree of identity with another amino acid sequence has the same degree of homology to a specified amino acid sequence.

In the present context a derivative is intended to be a protein having equivalent activity and/or a functional equivalent activity to an antisecretory factor as defined herein, being derived from another substance either directly or by modification or partial substitution, wherein one or more amino acids have been substituted by another amino acid, which amino acid can be a modified or an unnatural amino acid. For example, the antisecretory factor derivatives according to the invention may comprise an N terminal and/or a C terminal protecting group. One example of an N terminal protecting group includes acetyl. One example of a C terminal protecting group includes amide.

By proteins, homologues, derivatives, peptides and/or fragment thereof having an amino acid sequence at least, for example 95% identical to a reference amino acid sequence it is intended that the amino acid sequence of e.g. the peptide is identical to the reference sequence, except that the amino acid sequence may include up to 5 point mutations per each 100 amino acids of the reference amino acid sequence. In other words, to obtain a polypeptide having an amino acid sequence at least 95% identical to a reference amino acid sequence, up to 5% of the amino acids in the reference sequence may be deleted or substituted with another amino acid, or a number of amino acids up to 5% of the total amino acids in the reference sequence may be inserted into the reference sequence. These mutations of the reference sequence may occur at the amino or carboxy terminal positions of the reference amino acid sequence or anywhere between those terminal positions, interspersed either individually among amino acids in the reference sequence or in one or more contiguous groups within the reference sequence.

In the present invention, a local algorithm program is best suited to determine identity. Local algorithm programs, (such as Smith Waterman) compare a subsequence in one sequence with a subsequence in a second sequence, and find the combination of subsequences and the alignment of those subsequences, which yields the highest overall similarity score. Internal gaps, if allowed, are penalized. Local algorithms work well for comparing two multidomain proteins, which have a single domain, or just a binding site in common.

Methods to determine identity and similarity are codified in publicly available programs. Preferred computer program methods to determine identity and similarity between two sequences include, but are not limited to, the GCG program package (Devereux, J et al (1994)) BLASTP, BLASTN, and FASTA (Altschul, S. F. et al (1990)). The BLASTX program is publicly available from NCBI and other sources (BLAST Manual, Altschul, S. F. et al, Altschul, S. F. et al (1990)). Each sequence analysis program has a default scoring matrix and default gap penalties. In general, a molecular biologist would be expected to use the default settings established by the software program used.

The antisecretory proteins or a peptide or a homologue, derivative and/or fragment thereof having equivalent activity as defined herein, can comprise 4 amino acids or more, such as 5-16 amino acids, such as 5, 6, 7, 8, 9, 10, 11, 12, 13, 14, 15, 16, 17, 18, 19 or 20 amino acids or more. In other preferred embodiments the antisecretory factor consists of 42, 43, 45, 46, 51, 80, 128, 129 or 163 amino acids. In preferred embodiments the antisecretory factor consists of 5, 6, 7, 8 or 16 amino acids.

In another preferred embodiment, the antisecretory proteins or a peptide or a homologue, derivative or fragment thereof having equivalent activity according to the present invention consists of a sequence according to the following formulae:

X1-V-C-X2-X3-K-X4-R-X5    (SEQ ID NO: 7)

wherein X1 is I, amino acids 1-35 of SEQ ID NO: 6, or is absent, X2 is H, R or K, X3 is S or L, X4 is T or A, X5 is amino acids 43-46, 43-51, 43-80 or 43-163 of SEQ ID NO: 6, or is absent.

The antisecretory factor according to the present invention, can be produced in vivo or in vitro, e.g. recombinantly, synthetically and/or chemically synthesized, and/or isolated from a naturally occurring source of antisecretory factors, such as from pig pituitary glands or bird's eggs. After production, the antisecretory factors may be further processed, such as by chemical or enzymatic cleavage to smaller antisecretory active fragments or by modification of amino acids. It is presently not possible to obtain antisecretory factor in pure form by purification. It is however possible to produce a biologically active antisecretory factor protein recombinantly or synthetically as previously disclosed in WO 97/08202 and WO 05/030246. WO 97/08202 also discloses the production of biologically active fragments of this protein of 7-80 amino acids. The antisecretory factor according to the invention may further comprise an N terminal and/or a C terminal protecting group. One example of an N terminal protecting group includes acetyl. One example of a C terminal protecting group includes amide.

In a preferred embodiment of the present invention the antisecretory factor is a selected among SEQ ID NO 1-6, i.e. VCHSKTRSNPENNVGL (SEQ ID NO 1, in this context also called AF-16), IVCHSKTR (SEQ ID NO 2), VCHSKTR (SEQ ID NO 3), CHSKTR (SEQ ID NO 4), HSKTR (SEQ ID NO 5), or the amino acid sequence of an antisecretory protein according to SEQ ID NO 6 using the common one letter abbreviations for amino acids. SEQ ID NO 1, 2, and 3 have previously been disclosed in e.g. WO 05/030246. As specified in the accompanying sequence listing, some of the amino acids in the above-specified sequences may be replaced by other amino acids. In the following, the position of a particular amino acid in a particular amino acid sequence is calculated from the left, denoting the most N-terminal amino acid as being in position 1 in that particular sequence. Any amino acid substitution(s) as specified below may be performed independently of any other amino acid substitution(s) in that sequence. In SEQ ID NO 1, the C in position 2 may be replaced by S, H in position 3 may be replaced with R or K, S in position 4 may be replaced with L, and/or T in position 6 may be replaced with A. In SEQ ID NO 2, C in position 3 may be replaced by S, H in position 4 may be replaced by R or K, S in position 5 may be replaced by L, and/or T in position 7 may be replaced by A. In SEQ ID NO 3, C in position 2 may be replaced by S, H in position 3 may be replaced by R or K, S in position 4 may be replaced by L, and/or T in position 6 may be replaced by A. In SEQ ID NO 4, C in position 1 may be replaced by S, H in position 2 may be replaced by R or K, S in position 3 may be replaced by L, and/or T in position 5 may be replaced by A. In SEQ ID NO 5, H in position 1 may be replaced by R or K, S in position 2 may be replaced by L, and/or T in position 4 may be replaced by A.

Also intended by the present invention is the combination of two or more of any of the fragments according to SEQ ID NO 1-6.

In one embodiment of the present invention, the pharmaceutical composition according to the invention further comprises a pharmaceutically acceptable excipient. The choice of pharmaceutically acceptable excipient and their optimum concentration for use according to the present invention can readily be determined by the skilled person by experimentation. Pharmaceutically acceptable excipients for use according to the present invention include solvents, buffering agents, preservatives, chelating agents, antioxidants, and stabilizers, emulsifying agents, suspending agents and/or diluents. The pharmaceutical compositions of the invention may be formulated according to conventional pharmaceutical practice, e.g. according to "Remington: The science and practice of pharmacy", 21st edition, ISBN 0-7817-4673-6 or "Encyclopedia of pharmaceutical technology", 2nd edition, ed. Swarbrick J., ISBN: 0-8247-2152-7. A pharmaceutically acceptable excipient is a substance that is substantially harmless to the individual to which the composition is to be administered Such an excipient normally fulfils the requirements given by the national health authorities. Official pharmacopoeias such as e.g. the British Pharmacopoeia, the United States of America Pharmacopoeia and The European Pharmacopoeia set standards for pharmaceutically acceptable excipients.

The following is a review of relevant compositions for optional use in a pharmaceutical composition according to the invention. The review is based on the particular route of administration. However, it is appreciated that in those cases where a pharmaceutically acceptable excipient may be employed in different dosage forms or compositions, the application of a particular pharmaceutically acceptable excipient is not limited to a particular dosage form or of a particular function of the excipient. It should be emphasized that the invention is not limited to the use of the compositions mentioned in the following.

Parenteral Compositions:

For systemic application, the compositions according to the invention may contain conventional non-toxic pharmaceutically acceptable carriers and excipients, including micro spheres and liposomes.

The compositions for use according to the invention may include all kinds of solid, semisolid and fluid compositions.

The pharmaceutically acceptable excipients may include solvents, buffering agents, preservatives, chelating agents, antioxidants, and stabilizers, emulsifying agents, suspending agents and/or diluents. Examples of the different agents are given bellow.

Example of Various Agents:

Examples of solvents include but are not limited to water, alcohols, blood, plasma, spinal fluid, ascites fluid and lymph fluid.

Examples of buffering agents include but are not limited to citric acid, acetic acid, tartaric acid, lactic acid, hydrogen phosphoric acid, bicarbonates, phosphates, diethylamide, etc.

Examples of chelating agents include but are not limited to EDTA and citric acid.

Examples of antioxidants include but are not limited to butylated hydroxyl anisole (BHA), ascorbic acid and derivatives thereof, tocopherol and derivatives thereof, cysteine, and mixtures thereof.

Examples of diluents and disintegrating agents include but are not limited to lactose, saccharose, emdex, calcium phosphates, calcium carbonate, calcium sulphate, mannitol, starches and microcrystalline cellulose.

Examples of binding agents include but are not limited to saccharose, sorbitol, gum acacia, sodium alginate, gelatine, chitosan, starches, cellulose, carboxymethylcellulose, methylcellulose, hydroxypropylcellulose, polyvinylpyrrolidone and polyethyleneglycol.

The pharmaceutical composition according to the invention can in one context be administered locally or via intravenous peripheral infusion or via intramuscular or subcutaneous injection into the patient or via buccal, pulmonary, nasal, cutaneous or oral routes. Furthermore, it is also possible to administer the pharmaceutical composition through a surgically inserted shunt into a cerebral ventricle of the patient.

In one embodiment, the pharmaceutical composition used according to the present invention is formulated for intraocular, local, intranasal, oral, subcutaneous and/or systemic administration.

In a preferred embodiment, the composition of the invention is administrated by application as a suspension or, even more preferably, a powder for inhalation with a spray, aerosol, inhaler or nebulizer nasally and/or to the respiratory tract.

The administration of a powder comprising antisecretory factors has additional advantages in terms of stability and dosage. A pharmaceutical composition according to the invention can also be topically applied, intraocularly, intranasally, orally, subcutaneously and/or systemically administered via blood vessels. In a preferred embodiment, the pharmaceutical composition is formulated for intravenous, intramuscular, local, oral or nasal administration. Typically, when used for topical application to the eye, the applied concentration in the composition of the invention is from 1 µg to 1 mg per application, preferably 50-250 µg, either as a single dose per day or repeated several times per day (multiple doses), but is not limited thereto.

Systemically administered to the blood, the dose is within the range of 0.1 µg to 10 mg per application and kg body weight, such as 0.1 µg to 1 mg per application and kg body weight, preferably 1-500 pg/kg body weight, preferably again 1-50 pg/kg body weight either as a single dose per day or repeated several times per day. When egg yolk enriched in antisecretory factors is used according to the present invention, this formulation is preferably administered orally.

Accordingly, the present invention relates to the use of an antisecretory protein or a derivative, homologue, and/or fragment thereof, having equivalent activity, and/or a pharmaceutically active salt thereof, for the manufacture of a pharmaceutical composition and/or a medical food for the treatment and/or prevention of dysfunction of lipid rafts and/or caveolae. In one embodiment, said antisecretory protein consists of a sequence according to the following formula

```
X1-V-C-X2-X3-K-X4-R-X5           (SEQ ID NO: 7)
``` wherein X1 is I, amino acids 1-35 of SEQ ID NO: 6, or is absent, X2 is H, R or K, X3 is S or L, X4 is T or A, X5 is amino acids 43-46, 43-51, 43-80 or 43-163 of SEQ ID NO: 6, or is absent. In another embodiment, the invention relates to the use of an antisecretory protein which comprises an amino acid sequence as shown in SEQ ID NO: 1. In another embodiment, the invention relates to the use of an antisecretory protein which comprises an amino acid sequence as shown in SEQ ID NO: 2. In yet another embodiment, the invention relates to the use of an antisecretory protein which comprises an amino acid sequence as shown in SEQ ID NO: 3. In yet another embodiment, the invention relates to the use of an antisecretory protein which comprises an amino acid sequence as shown in SEQ ID NO: 4. In a yet further embodiment, the invention pertains to the use or an antisecretory protein which comprises an amino acid sequence as shown in SEQ ID NO: 5.

Furthermore, in yet another embodiment, the invention pertains to the use of an antisecretory protein which is a protein with an amino acid sequence as shown in SEQ ID NO 6, or a homologue, derivative and/or fragment thereof comprising amino acids 38-42 of SEQ ID NO 6. In yet another embodiment, the invention relates to the use of a pharmaceutical composition as disclosed herein, which comprises two or more antisecretory proteins selected from the proteins as disclosed in SEQ ID NO: 1-6, and SEQ ID NO 6 or a homologue, derivative and/or fragment thereof comprising amino acids 38-42 of SEQ ID NO 6, or a sequence as disclosed by the general formulae described herein. Said sequences are all equally preferred to be used in the present invention.

In one embodiment of the invention, said pharmaceutical composition further comprises a pharmaceutically acceptable excipient. Such an excipient may be any preferable excipient chosen to be appropriate for the specific purpose. Examples of excipients are disclosed herein.

In another embodiment of the invention, said pharmaceutical composition is formulated for intraocular, intranasal, oral, local, subcutaneous and/or systemic administration. The chosen route of administration will vary depending on the condition of the patient to be treated and the patient's age and gender etc.

In another embodiment, the pharmaceutical composition is formulated for administration as a spray, aerosol or by a nebulizer or an inhaler. In yet another embodiment, the invention relates to a pharmaceutical composition and/or a medical food which is formulated for administration systemically to the blood at a dose of 0.1 µg to 10 mg per application and kg body weight and day, such as 0.1 µg to 1 mg per application and kg body weight and day, preferably 1-500 µg per application and kg body weight and day, preferably again 1-50 µg per application and kg body weight and day. In another embodiment, said dose is 1-1000 µg per application and kg body weight and day, such as 1-100 µg per application and kg body weight and day. The amount of the pharmaceutical composition which is distributed to the patient in need thereof will of course vary depending on the patient to be treated, and will be decided by the skilled person, such as a medical practitioner, for each occasion. Said administration can be performed either as a single dose or as multiple daily applications.

Over the past years, it has become increasingly apparent, that lipid rafts, caveolae and caveolins are involved in several human disease states, such as, but not limited to muscular dystrophy (e.g. limb girdle muscular dystrophy), imbalance in cellular cholesterol (e.g. Niemann-Pick type C), and/or dysfunction in the generation of the amyloid peptide from the amyloid precursor protein (APP) (e.g. Alzheimer's disease). The present invention thus in one embodiment also provides the use of a pharmaceutical compositions as described herein for use in preventing and/or treating muscular dystrophy, imbalance in cellular cholesterol, and/or dysfunction in the generation of the amyloid peptide from the amyloid precursor protein.

Lipid rafts represent a type of cellular domain wherein lipids of specific chemistry may dynamically associate with each other, to form platforms important for membrane protein sorting and construction of mass transfer and signaling complexes.

Several cellular receptors are known to reside in lipid rafts and/or caveolae of the cellular membrane, e.g. it has been demonstrated that rafts are important in the regulation of GPCRs at all of the stages of their lifecycle, i.e. in the exocytic pathway, in the plasma membrane, and in the endocytic pathway. Lipid rafts and/or caveolae are found to be involved in the regulation of receptor stability, regulating signaling and trafficking of any particular GPCR. The rapid turn-over of receptors, ion channel and water channel proteins and other signal transducers may further be monitored. Consequently, in one embodiment, the present invention relates to the use of a pharmaceutical composition according to the present invention for regulating receptor stability, regulating signaling and/or trafficking of one or more receptors localized in the cell membrane.

Many receptors have an average life-span of no more than 3-5 hours. In consequence, a constant production of new receptor proteins requires that the produced receptor proteins are securely and correctly guided and fixed at the appropriate locations in the cell membrane. The present invention discloses a potential use of a pharmaceutical composition according to the present invention for improving and/or facilitating such a receptor positioning in the cell membrane. What is more, recent findings indicate that classical steroid hormone receptors reside in lipid rafts and/or caveolae in the cell membrane, and thus may function within and with the help of these structures. Examples of such receptors, but not limited to, are receptor tyrosine kinases, i.e. EGFR and androgen receptor signaling pathways, Akt1, IL-6, STAT3, estrogen receptors (ER). Thus, the present invention also provides for the use of a pharmaceutical composition according to the present invention or treating and/or preventing conditions associated with dysfunctions of steroid hormone receptors.

Insulin resistance, defined as the decreased ability of cells or tissues to respond to physiological levels of insulin, is thought to be the primary defect in the pathophysiology of type II diabetes. TNFa is known to play a major role in this resistance, as are other cytokines and lymphokines likely to do. Currently, it has become clear that the hormone's unique actions are closely connected to the compartmentalization of the signaling molecule in lipid rafts in the cell membrane. Thus, proper function of lipid rafts has been shown to be critical for proper compartmentalization of insulin signaling e.g. in apidocytes. A disruption of lipid raft organization and/or function leading to the inhibition and/or disruption of insulin's metabolic signaling, is probably at least partially due to aberrant expression of glycosphingolipids. In a currently preferred embodiment, the present invention thus relates to the use of a pharmaceutical composition comprising an antisecretory protein or a derivative, homologue, and/or fragment thereof, having equivalent activity, and/or a pharmaceutically active salt thereof for normalizing insulin's metabolic signaling. The invention consequently in said embodiment also relates to treating and/or preventing diabetes mellitus, e.g. diabetes type II.

Lipid rafts and caveolae act as organized centers for signal transduction. Both the insulin receptor and TC10 reside in lipid rafts. The mistargeting of TC10 to a non-lipid raft domain prevents its activation by insulin and blocks insulin action. Numerous studies have demonstrated that lipid rafts act as organizing centers for insulin signaling in the apidocyte. The activated insulin receptor specifically catalyzes the tyrosine phosphorylation of certain proteins in lipid rafts, including caveolin and Cbl. Components of insulin signaling are constitutively localized in lipid rafts, including some or all of the insulin receptor, flotillin, and TC10.

Insulin stimulates glucose transport in fat and muscle cells through a process of regulated vesicle recycling in which the facilitative glucose transporter Glut4 is translocated from intracellular sites to the plasma membrane. In unstimulated cells, Glut4 undergoes endocytosis into endosomes and subsequently sorts into specialized storage vesicles that traffic to plasma membrane after activation of the insulin receptor. The vesicles then dock and fuse at specific sites at the membrane, resulting in extracellular exposure of the transporter. The signaling cascade from the insulin receptor involves tyrosine phosphorylation of a number of intracellular substrates and activation of the P13-kinase pathway and the activation of a G-protein, which in turn binds to numerous effectors, including the exocyst protein Exo70.

What is more, the exocyst complex, comprising Exo70, Sec6, and Sec8, is involved in the compartmentalization of Glut4-containing vesicles at lipid raft domains in the cell membrane, e.g. in adipocytes. Parts of the exocyst complex are recruited by G-proteins after activation by insulin and are essential for insulin-stimulated glucose uptake in cells. Moreover, it has of lately been shown that their targeting to lipid rafts is required for glucose uptake and Glut4 docking at the plasma membrane. Curiously, this complex also requires a PDZ domain protein, which binds to the complex upon its translocation to the lipid raft. Exocyst assembly at lipid rafts sets up target sites for Glut4 vesicles, which transiently associate with these micro domains upon stimulation of cells with insulin.

As has been demonstrated in the experimental section of this application, the inventors have now been able to show that antisecretory factors exert beneficial effects on the development of symptoms at chemically induced diabetes mellitus. In detail, experimentally induced diabetes mellitus caused by treatment with streptozocin was investigated with regard to whether it was beneficially affected by treatment with AF-16. In a presently preferred embodiment, the present invention therefore relates to the use of a pharmaceutical composition comprising an antisecretory protein or a derivative, homologue, and/or fragment thereof, having equivalent activity, and/or a pharmaceutically active salt thereof for treating and/or preventing medical conditions in a patient that are associated with diabetes mellitus and/or diabetes related complications, such as selected from diabetes I and II.

In a further preferred embodiment of the present invention, the pharmaceutical composition according to the invention is employed for normalizing lipid raft formation and/or function in muscle cells, endothelial cells, fatty cells and/or red blood cells, for treating and/or preventing dysfunction of Glut4 and/or exocyst assembly in said cells. Consequently, said pharmaceutical composition is herein used for treating and/or preventing diabetes mellitus and/or diabetes related complications, such as selected from diabetes I and II.

Caveolae are dynamic structures that can bud from the plasma membrane, forming cytoplasmic vehicles involved both in receptor-mediated uptake of solutions into the cell as well as in transcytosis through the cell. Although caveolae are found in many cell types, they are especially abundant in adipocytes, where they can be clustered into ringlike structures (caveolae rosettes) often associated with actin filaments. They are involved in fatty acid uptake as well as in fatty acid transport and/or fatty acid binding of the cells. Furthermore, caveolae and calveolin-1 are well characterized to be involved in cholesterol transport to the cell surface and to be regulated by cholesterol levels in the cell. Thus, the present invention in a further embodiment also relates to the use of a pharmaceutical composition comprising an antisecretory protein or a derivative, homologue, and/or fragment thereof, having equivalent activity, and/or a pharmaceutically active salt thereof for treating and/or preventing medical conditions in a patient that are associated with dysfunctions in fatty acid uptake, fatty acid transport, fatty acid binding and/or cholesterol levels.

Caveolae dysfunctions are associated with several human diseases. E.g. Caveolin-1 (CAV1)-null cells show increased proliferation, and loss of CAV-accelerates tumour genesis. In some breast cancers, CAV1 is down regulated and a number of sporadic mutations in CAV1 have been detected in samples of human breast cancers, correlating specifically with estrogen-receptor-alpha-positive status. CAV3, the muscle-specific caveolin isoform is also strongly linked to disease. Many mutations in CAV3 are associated with a number of human muscle disorders.

In another, equally preferred embodiment, the pharmaceutical composition according to the invention is employed for normalizing caveolae build up and/or function to counteract and/or stabilize high blood pressure in a patient in need thereof. As is demonstrated in the experimental section, treatment of mammals with a pharmaceutical composition according to the present invention can reduce complications due to hyperotony both in the small and large circulation system of the mammalian body. Thus, the present invention can be employed to treat and/or prevent heart attack, high blood pressure, lung diseases, plaque formation and/or traumatic injury to the vascular system, such as of the heart and lungs as well as hormonal dysfunction and dysregulation.

In another aspect, the present invention relates to a method for the treatment and/or prevention of dysfunction of lipid rafts and/or caveolae in a mammal in need thereof, said method comprising administering an effective amount of a pharmaceutical composition comprising an antisecretory protein or a derivative, homologue, and/or fragment thereof, having equivalent functional activity, and/or a pharmaceutically active salt thereof. In one embodiment, the invention relates to a method, wherein said antisecretory protein consists of a sequence according to the following formula X1-V-C-X2-X3-K-X4-R-X5 (SEQ ID NO: 7) wherein X1 is I, amino acids 1-35 of SEQ ID NO: 6, or is absent, X2 is H, R or K, X3 is S or L, X4 is T or A, X5 is amino acids 43-46, 43-51, 43-80 or 43-163 of SEQ ID NO: 6, or is absent. In another embodiment, the present invention relates to a method, wherein said antisecretory protein comprises an amino acid sequence as shown in SEQ ID NO: 1. In yet another embodiment, the present invention relates to a method, wherein said antisecretory protein comprises an amino acid sequence as shown in SEQ ID NO: 2. In yet another embodiment, the invention relates to a method, wherein said antisecretory protein comprises an amino acid sequence as shown in SEQ ID NO: 3. Furthermore, the invention relates to a method wherein said antisecretory protein comprises an amino acid sequence as shown in SEQ ID NO: 4. In yet another embodiment, the present invention relates to a method wherein said antisecretory protein comprises an amino acid sequence as shown in SEQ ID NO: 5. In yet another embodiment, the invention pertains to a method, wherein said antisecretory protein is a protein with an amino acid sequence as shown in SEQ ID NO: 6, or a homologue, derivative and/or fragment thereof comprising amino acids 38-42 of SEQ ID NO: 6. In one embodiment, the invention relates to a method, wherein said pharmaceutical composition comprises two or more antisecretory proteins selected from the proteins SEQ ID NO: 1-6, and SEQ ID NO: 6 or a homologue, derivative and/or fragment thereof comprising amino acids 38-42 of SEQ ID NO: 6, or a sequences as described by the general formula herein. In one embodiment, said pharmaceutical composition is formulated for intraocular, intranasal, oral, local, subcutaneous and/or systemic administration. In yet another embodiment, said pharmaceutical composition and/or medical food is formulated for administration as a spray, aerosol, or by a nebulizer or an inhaler. Also encompassed by an embodiment of the present invention, is a method, wherein the pharmaceutical composition is formulated for administration systemically to the blood at a dose of 0.1 μg to 10 mg per application and kg body weight and day, such as of 0.1 μg to 1 mg per application and kg body weight and day, preferably 1-500 μg per application and kg body weight and day, preferably again 1-50 μg per application and kg body weight and day. In one embodiment of said method, said administration is performed either as a single dose or as multiple daily applications. The present invention also relates to a method for the treatment and/or prevention of dysfunction of lipid rafts and/or caveolae in a mammal in need thereof, said method comprising administering an effective amount of a pharmaceutical composition comprising an antisecretory protein or a derivative, homologue, and/or fragment thereof, having equivalent functional activity, and/or a pharmaceutically active salt thereof.

In one preferred embodiment, the present invention also relates to a method for the treatment and/or prevention of dysfunction of lipid rafts and/or caveolae in a mammal in need thereof, said method comprising administering an effective amount of a pharmaceutical composition comprising an antisecretory protein or a derivative, homologue, and/or fragment thereof, having equivalent activity, and/or a pharmaceutically active salt thereof.

It is furthermore to be understood and clear that a method comprising administering an effective amount of a pharmaceutical composition to a mammal in need thereof and/or the second medical use of a pharmaceutical composition comprising an antisecretory protein or a derivative, homologue, and/or fragment thereof, having equivalent activity, and/or a pharmaceutically active salt thereof, according to the present invention, is directed to all conditions described herein to be associated with dysfunction of lipid rafts and/or caveolae.

EXPERIMENTAL SECTION

Example 1

Adolescent and adult rats, with a body weight of 150-300 g and of either sex, were treated experimentally to induce pulmonary hypertension and reactive alterations in the lungs. Pulmonary hypertension (PH) is defined as having a pressure in excess of the normal pulmonary artery pressure, ~20 mm Hg, usually in the range of 30-40 mm Hg. It is a progressive disease with high morbidity and mortality in humans as well as in animals. Experimental models enable investigation of the initiating mechanisms. A single treatment of rats with monocrotaline is an established approach for the induction of PH (Cf. Mathew et al., 2004). This plant alkaloid is activated in the liver to pyrrolic metabolites, with a half-life of just a few seconds and therefore mainly affects the pulmonary arterial endothelium, causing endothelial cell damage and pulmonary vascular leak. This is followed within the next few days by a prominent stimulation of pulmonary arterial endothelial cell DNA synthesis and hypertrophy. These endothelial cells are thought to secrete growth and motility promoting factors, which contribute to the migration and reactive changes of adjacent smooth muscle cells. Within two weeks, the right heart ventricle turns hypertrophic due to the elevated load resulting from the crotaline-induced changes in the pulmonary vascular system.

Groups of Sprague-Dawley rats had a single intraperitoneal injection of crotaline (60 mg/kg body weight; Sigma). Every second animal had an Alzet osmotic minipump (type 2001; fill volume—235 μL; pumping rate—1 μL/h; pre-started; fill solution containing 20 mg/mL of AF-16 dissolved in PBS with 15% ethanol added) implanted subcutaneously in its back. The pump was thus delivering ~20 μg AF-16 per hour for at least 10 days. In one experiment the rats with Alzet 2001 pump got at the implantation as well a single intramuscular injection of 2 mg AF-16. For comparison, every second rat had at the crotaline injection Alzet 2001 pumps implanted filled with the vehicle, PBS with 15% ethanol. Additional groups of weight-matched rats had just pumps filled with either AF-16 or the vehicle implanted but received no crotaline.

The rats were anaesthetized 18 days later, and their body weights determined. Those treated with crotaline were lean and small for their age, were less active and had a ruggy fur, and had a low weight, as compared to the untreated normal controls. Those treated with crotaline and having had AF infused with the aid of minipumps appeared healthy and had almost the same weight and appearance as the controls. The pressure in the right heart ventricle was assessed with the aid of a fiber optic miniature transducer system (Samba System 3200 & Samba Preclin 420 sensor; Samba Sensors AB, V. Frolunda, Sweden), inserted through the right jugular vein. The mean pulmonary arterial blood pressure was about 20 mm Hg in the rats treated with the vehicle or having been treated with AF-16. In contrast, rats treated with crotaline (single ip injection; 60 mg/kg body weight; crotaline dissolved in PBS) and the vehicle delivered by a Alzet pump had for 18 days an pulmonary artery pressure in excess of 30 mm Hg and a hypertrophy of the right ventricle, as assessed by comparing its wet weight to that of the left ventricle and with the weight of corresponding structures of non-treated, normal rats. Treatment with AF-16 of the crotaline treated rats turned the right ventricular blood pressure and the lung arterial blood pressure close to normal and there was no significant hypertrophy of the right ventricle, as compared to that of normal non-treated rats. These results were reproducible, as consistently achieved when repeated. It is known that crotaline derived compounds cause disruption of e.g. the protein caveolin, resulting in disorganization of the caveolae and lipid rafts, which effects account for alterations in the endothelial cell signalling in this model of PH (Mathew R, et al., 2004).

We conclude that treatment with AF-16 abolished the rebuilding of the pulmonary vascular system and thus the development of pulmonary abnormalities and right heart hypertrophy otherwise documented after treatment with crotaline. The induced damage to the lipid rafts and the caveolae in the endothelium and the vascular smooth muscle cells and the subsequent reactive changes were thus reduced by treatment with AF-16, and did neither result in the expected vascular abnormalities, nor in the right heart ventricular hypertrophy.

Example 2

In a second experiment it was investigated whether the administration of AF-16, at a dose demonstrated above to abolish the development of pulmonary hypertension, affected the healing process of injured arteries.

Anaesthetized adult rats had an osmotic minipump (Alzet type 2001; fill volume—235 µL; pumping rate —1 µL/h; prestarted; fill solution containing 10 mg/mL of AF-16 dissolved in PBS with 15% ethanol added) implanted subcutaneously in its back. In addition 1 mg AF-16 was injected intramuscularly just after the implantation. Thereafter, the skin in the right groin was shaved, cut through and the right femoral and common iliac artery was isolated. A Pean's forceps was positioned around the artery and closed three times, each time for 15 seconds, and then removed. Great care was taken not to perforate the vessel or any neighboring structures. The patience of the femoral and iliac arteries and the veins were checked to ensure appropriate blood circulation. The margins of the wound were then adapted and sutured. In parallel, additional rats had their right femoral and iliac artery clamped, but had the vehicle, PBS with 15% ethanol, infused instead of the active substance.

After 10 days, the animals were once more anesthetized, and 1 ml/kg body weight of a mixture of 2% Evans blue and 3% albumin (bovine serum albumin: Sigma), dissolved in PBS was infused. After 15 minutes, the animal was fixed by transcardial perfusion with a buffered formalin-saline solution after an initial rinse with PBS with heparin added. The right and left iliac and femoral arteries were carefully isolated and attached at their ends, immersed in a formalin solution in PBS. After 1 hour, the vessels were opened longitudinally with a fine scissor and observed with regard to prevalence of blue staining of the luminal surface of the arterial wall. The untouched arteries showed no staining of their luminal surface. In contrast, those that had had their right iliac and femoral artery traumatized and had been treated with the vehicle displayed continuous, distinct, intense blue staining of the entire injured vessel wall, with fairly distinct borders. The traumatized iliac and femoral arteries from the third group of animals, treated with AF-16 since the injury, had spot-like dots and irregularly shaped, discontinuous areas that were blue stained, separated by seemingly unstained areas within the damaged vessel zone. As judged visually, more than half on the area within the injured zone were unstained in those treated with AF-16. That meant that AF-16 promoted the recovering of the initially denuded, inner wall of the vessel, turning it lined by cells. Further, there was less visible clot to be observed, as compared to the vessels that had been injured in animals treated with the vehicle. Light microscopy of the injured areas revealed that the number of leukocytes, platelets, macrophages and foam cells on and in the injured tissue was less after AF-16 treatment as compared to that after treatment with the vehicle. Further, there were less mononuclear cells attached to the surface. Smooth muscle cells were recognized invading the adluminal layer, but to a lesser extent after AF-16 treatment as compared to that after vehicle. Endothelial cells, fibroblasts and smooth muscle cells are under normal circumstances characterized by having an abundance of caveolae and vesicles at and in their plasma membrane. These surface structures are deranged at and after the mechanical trauma to the blood vessel and remain to a considerable extent so for at least 10 days, i.e. the time period investigated in the presented experiments. However, in animals treated with AF-16 there is a prominent tendency to normalization, as compared to the conditions prevalent in those treated with the vehicle. The signal transduction for the above mentioned cell types are known to largely be mediated through the lipid rafts and caveolae. It is thus concluded that treatment with AF-16 reduces the inflammatory and reactive alterations in the injured blood vessels and normalizes to a considerable extent the structure and function of cells in such areas. AF-16 is exerting its beneficial effects by interfering with lipid rafts and caveolae.

Example 3

In an experiment it was investigated whether the administration of AF-16 affected the healing process of injured skin and cartilage, using freeze-thaw injury to a rat ear as a model system. Anaesthetized adult rats had an osmotic minipump (Alzet type 2001; fill volume—235 µL; pumping rate—1 µL/h; prestarted; fill solution containing 20 mg/mL of AF-16 dissolved in PBS with 15% ethanol added) implanted subcutaneously in its back. In addition 1 mg AF-16 was injected intramuscularly just after the implantation of the pump. Thereafter, a freeze-thaw injury was applied by compressing the ear in a standardized manner with the aid of a Pean's forceps, chilled in liquid nitrogen. For comparison, additional rats were treated in the same way in parallel were treated with the vehicle, PBS with 15% ethanol, only and no peptide. Additionally, normal rats, which had not been exposed to any freeze-thaw injury, were used for reference as were non-injured rats having pumps with AF-16 implanted.

Rats treated for 2 weeks with AF-16 after the freeze-injury showed less edema and inflammation as compared to those injured but treated with the vehicle. On either side bordering the injured elastic cartilage in the ear there was a formation of new hyaline cartilage. The AF-16 treated rats had at 2 weeks less remaining necrosis in the remaining elastic cartilage, less prominent formation of enclosing hyaline cartilage, less edema and infiltration of inflammatory cells. The amount of collagen and density of inflammatory cells were reduced in the AF-16 treated animals as compared to those having had the vehicle. Treatment of non-injured rats with either the vehicle or AF-16 did not alter the structures in the ear.

It is concluded that the fate of the healing process regarding injured skin and underlying cartilage was more beneficial and resulted in the formation of less scar tissue if the animals were treated with AF-16. The freeze injury much more prominently reduced the number of caveolae in cells in the injured areas in the vehicle treated ears as compared to that observed in those having had AF-16.

Example 4

Adult rabbits were investigated with regard to whether the administration of AF-16 affected the healing process of injured skin and periost.

Anaesthetized adult New Zeeland albino rabbits (female, body weight 2.5-2.8 kg) had a helmet, made of glass fiber reinforced plastic, glued to the surgically exposed skull bone. The rabbits had either AF-16 or the vehicle injected intravenously in a marginal ear vein. The dose of AF-16 was up to 5 mg per kg body weight, twice daily. The calvarial skin wound and the injection sites in the ear were investigated macroscopically after a week. Then, specimens were dissected from both areas and prepared by fixation, embedding, sectioning and staining for light microscopic examination. Treatment with AF-16 resulted in the prevalence of less edema in the healing skin, which further was less inflamed and lacked the prominent, hypertrophic scar tissue demonstrable in the corresponding specimens from the vehicle treated animals. Light microscopy confirmed that the specimens from AF-16 treated animals had less inflammatory cells and less collagen as compared to the vehicle treated ones. Further, in specimens from the AF-16 treated animals the blood vessels appeared more mature.

It is concluded that AF-16 improved the healing of deep skin wounds, reducing the otherwise marked inflammation and the prevalence of edema and excessive scar tissue. The AF treatment appeared to turn the reduced frequency of caveolae more normal than observed among the vehicle treated ones.

Example 5

Adult rats have been investigated with regard to whether the healing of experimentally induced gastric wounds was influenced by the administration of AF-16.

Anaesthetized rats had an osmotic minipump (Alzet type 2001; fill volume—235 µL; pumping rate—1 µL/h; prestarted; fill solution containing 20 mg/mL of AF-16 dissolved in PBS with 15% ethanol added) implanted subcutaneously in its back. In addition 2 mg AF-16 was injected intramuscularly just after the implantation of the pump. Thereafter, the abdomen was shaved and the abdominal wall surgically opened. The stomach was identified and its ventral aspects exposed, taking great care not to allow the adjacent, different organs and structures to dry or to mechanically be injured. Ventral aspects of the glandular (distal) part of the stomach were then exposed to 80% acetic acid, contained in a glass tube, for 60 seconds. Thereafter, the glass tube was rapidly removed and the exposed serosa were rinsed with large volumes of PBS. Sutures then closed the abdomen. In parallel other rats were treated in the same way but had the vehicle in the pump and got the same volume of the vehicle injected. After a week the rats were once more anaesthetized and the abdomen exposed and surgically opened. The prevalence of adhesions and of ascitis fluid was investigated, as was the healing of the gastric ulcer. There was less fluid in the abdominal cavity in those rats that had been treated with AF-16 as compared to those having had the vehicle. The extent of adhesions between the greater omentum and the stomach, intestine, spleen and liver as well as to the abdominal wall wound was less prominent and reduced in frequency and size in those treated with AF-16. Light microscopy confirmed the macroscopic impression of that the stomach wall was less edematous. The epithelial covering on the inner surface of the stomach was more complete and extensive, appearing better organized after AF-16 treatment. Further there was less infiltration of inflammatory cells in the gastric wall after AF-16 treatment. It is concluded that AF-16 improved the healing of the gastric wall wounds. Furthermore, the prevalence of ascites fluid was reduced as was the extent and severity of the abdominal adhesions.

Example 6

In another experiment it was investigated whether the administration of AF-16 affected the biointegration in a body of implanted foreign materials.

Anaesthetized adult rats had each an osmotic minipump (Alzet type 2001; fill volume 235 µL; pumping rate −1 µL/h; prestarted; fill solution containing 10 or 20 mg/mL of AF-16 dissolved in PBS with 15% ethanol added) implanted subcutaneously in its back. In addition 2 mg AF-16 was injected intramuscularly just after the implantation. The implants consisted of thin membranes (1×2 cm), sutures and foam (0.2× 0.5×1 cm; aimed for augmentation) all prepared of degradable polyurethane urea (Artelon®, obtained as a gift from Artimplant, V. Frölunda, Sweden). In parallel, additional rats had the same materials implanted at the same sites just beneath the muscle fascia on their back. The implantation procedure was performed as gently as possible to avoid bleedings and excessive tissue damage. Further, sponges of chitosan and chitosan membranes (Medicarb AB, Bromma, Sweden) were implanted as described above in rats either treated with the AF-16 or the vehicle.

When examined after 10 days, it was found that the biointegration of the implants was superior in those animals, which were treated with AF-16, both as judged macroscopically and by light microscopy of thin, stained sections. There were less inflammatory cells and macrophages along the borders of the implants, and fibroblasts were recognized to enter the foam implant, retrieved from the animals treated with AF-16. Additionally, the healing of the skin wound in the AF-16 treated rats appeared more mature with less reactive alterations, as compared to those treated with the vehicle. The signal transduction resulting in reactive tissue changes are known to involve the signal transfer through lipid rafts and caveolae of cells in the injured tissue.

Example 7

Experiments were performed to investigate whether the administration of AF-16 affected the ischemic reactions in an internal organ in a body.

Anaesthetized adult rats had an osmotic minipump (Alzet type 2001; fill volume—235 μL; pumping rate—1 μL/h; pre-started; fill solution containing 20 mg/mL of AF-16 dissolved in PBS with 15% ethanol added) implanted subcutaneously in its back. In addition 2 mg AF-16 was injected intramuscularly just after the implantation of the pumps. Ischemia was induced unilaterally in the left kidney by obstructing the blood flow through the renal artery for 40 minutes, and the subsequent recirculation. The right kidney was removed surgically during the clamping period. Thereafter, the wounds were closed and the animals received analgesics drugs but no additional treatment. In parallel, additional rats, receiving the vehicle but no peptide, were exposed to ischemia in the left kidney and had their right kidney removed. The animals were anaesthetized once more after either 4 or 7 days. The kidney was isolated, inspected, measured and weighed and the fixed in buffered formalin solution for further processing for light microscopy.

The experiments revealed that the ischemic and reactive alterations of the kidney were most prominent in the proximal tubules. There were less bleedings and necrosis in those treated with AF-16.

Example 8

Experiments have been performed with neoplastic tumors, investigated with regard to whether their growth was affected by treatment with AF-16.

Anaesthetized adult rats had an osmotic minipump (Alzet type 2001; fill volume—235 μL; pumping rate—1 μL/h; pre-started; fill solution containing 20 mg/mL of AF-16 dissolved in PBS with 15% ethanol added) implanted subcutaneously in its back. In addition, 2 mg AF-16 was injected intramuscularly just after the implantation of the pumps. The pumps were changed for new ones once a week. Different tumors, induced chemically or transplanted were investigated with regard to effects by AF-16 administration, as compared to treatment with the vehicle. Those rats that received a carcinogenic chemical developed smaller mammary tumors at a lower frequency after treatment with AF-16, as compared to vehicle treatment. The reactive and inflammatory changes were as well less prominent. Additional experimental tumors have as well been investigated, with beneficial effects achieved in those treated with AF-16, as compared to the vehicle.

Example 9

Experiments have been performed with rats with experimentally induced diabetes mellitus caused by treatment with streptozocin, investigated with regard to whether affected by treatment with AF-16.

Anaesthetized adult rats had an osmotic minipump (Alzet type 2001; fill volume—235 μL; pumping rate—1 μL/h; pre-started; fill solution containing 20 mg/ml of AF-16 dissolved in PBS with 15% ethanol added) implanted subcutaneously in its back. For comparison, additional rats were treated with the vehicle, but no peptide. A single dose of streptozocin (Sigma) was injected in the rats, and the appearance of glucose in the urine checked with commercial sticks and the appearance of elevated volumes of urine watched.

Treatment with AF-16 reduced according to our preliminary results the loss of urinary glucose and also reduced the urine volume. The blood glucose values appeared to be lower after AF-16. Thus, AF-16 exerts beneficial effects on the development of symptoms at chemically induced diabetes mellitus.

Example 10

Experiments are performed with AF, administrated to human subjects suffering from diabetes mellitus, type II. The study is blinded to the physician and to the patients. All patients have diabetes mellitus type II and are all thoroughly investigated for prevalence of other diseases than diabetes mellitus at the University Hospital in Lund, Sweden. The regional committee grants ethics permission. One group, x subjects, is given AF while x subjects in a second group for comparison have the same amount of control substance administered. After 12 weeks, blood samples are taken and analyzed.

A result to be observed is that the level of HbA1c is significantly reduced (p. 0.05), by 0.2 unites, for those having had AF as compared to those having had the non-active solution administered. This means that the blood glucose levels of the subjects having had AF remains at lower levels and are better controlled as compared to the conditions for those in the comparison (placebo) group. Thus, beneficial effects regarding the fate of the diabetes mellitus type II disease are achieved for those subjects having had AF.

Example 11

Oscillatory alterations in the calcium ion concentrations constitute a critical part of the signaling machinery in many types of cells, e.g. neurons, and astrocytes, prevalent in the brain, spinal cord and retina. Further, endocrine cells, such as pancreatic 6-cells have been disclosed to have a pulsatile insulin secretion. Endocrine pancreatic cells also shown to have related ion changes at e.g. the uptake of glucose. A slight disturbance of the astroglial cell's oscillations of calcium ions are considered to disturb the regulation of e.g. extracellular glutamate, which per se could lead to local microglial activation with the production of proinflammatory cytokines, astrocyte swelling, and, due to such swelling, decreased extracellular space and eventually brain damage. During these conditions, there is a decrease in both the glutamate release and the neuronal transmission. Tentatively, such a decreased transmission and disturbed activity in a brain is likely to be correlated to dysfunction of the nervous system and pathological psychoneurological activities and performance.

Experiments are performed to illustrate the calcium ion oscillations in astrocyte cells in nervous tissue. The oscillations is induced by a stimulant, e.g. histamine and/or a monoaminergic transmitter and the possibility to monitor the activity with specific proteins such as AF, is assessed. The local concentration of calcium ions is disclosed with the aid of calcium binding compounds, the fluorescence of which varies quantitatively and qualitatively with the concentrations of intracellular calcium ions. Fluorescence microscopy and confocal scanning microscopy of astrocytes and of neurons, mainly cultured in vitro, is utilized. Further electrophysiological approaches is used. Specified concentrations of AF is added to the cells in order to thereby assess effects on ion transporter systems, localized to lipid rafts in the cells. Further, different types of muscle cells and connective tissue cells is similarly assessed for prevalence, frequency and amplitude of calcium ion oscillations in their cytoplasm prior to, at and after the addition of AF and related compounds.

As can be seen in representative FIG. 1, the monitoring of calcium oscillations in a cell, tissue and/or organ does enable monitoring of such signaling event dysfunctions and aid in the normalization. Thereby dysfunctions and diseases treatments are possible.

Example 12

Aquaporins are a family of proteins, integrated in membranes, and expressed in all living cells and organisms. The major function of aquaporins is to control the water flow into and out of cells, i.e. between the cytoplasm of cells and the extracellular environment. Each type of cells, tissues and organs have their specific set of aquaporins with characteristic distribution patterns. Functional aquaporins are preferentially clustered in lipid rafts and caveolae, while subunits and dissociated aquaporin complexes may be demonstrable outside these membrane constituents. Performed experiments on brains and spinal cords have revealed that the expression and distribution of aquaporins, mainly aquaporin 1 and aquaporin 4, turned altered when exposed to ischemia or to distorsion and mechanical load. Further, at brain and spinal cord infections, e.g. encephalitis, the patterns of distribution and intensity of these two aquaporins became altered, as disclosed be immunohistochemistry and immunochemistry. The interaction between e.g. neurons and supporting glial cells and vascular structures seems to be intricate and complex, but important.

Experiments are performed mapping in more detail regarding effects of trauma, infections and other pathological conditions. Treatments with AF proteins, peptides, derivates and homologues are administrated, topically and systemically, delivered as a single dose, or by multiple applications or chronically, i.e. for the rest of the life of the treated subject. Effects are characterized quantitatively and qualitatively and the importance of effects on the structure and functions of the different types of aquaporins in a body. The experiments indicate that AF has a great impact in monitoring and even normalizing the prevalence, distribution and activity of aquaporins and ion channel complexes, which latter interact with the former ones. Thereby, new and important treatment approaches may be developed based on achieved results.

REFERENCES

1. Chini & Parenti, 2004
2. Dermine et al., 2001
3. Freeman et al., 2007
4. Graham D I & Lantos P L. Greenfield's Neuropathology, 7th ed., Arnold, London, 2002.
5. Head et al., 2006
6. Helms & Zurzolo, 2004
7. Kurzchalia & Parton, 1999
8. Lange S, & Lönnroth I. The antisecretory factor: synthesis, anatomical and cellular distribution, and biological action in experimental and clinical studies. Intern Rev. Cytology 210, 39-75, 2001.
9. Mahmutefendic et al., 2007
10. Marquez, D C et al., 2006
11. Mathew et al., 2004
12. Pollard, T D & Earnshaw, W C. Cell biology, Saunders, Philadelphia, 2002.
13. Petersen O H, Sutton R & Criddle D N. Failure of calcium microdomain generation and pathological consequences. Cell Calcium 40, 593-600, 2006
14. Pohl et al., 2004
15. Rajendran et al., 2007
16. Ross, M H & Pawlina, W. Histology, a text and atlas. Lippincott, Baltimore, 5th ed., 2006
17. Rutter G A, Tsuboi T & Ravier M A. $Ca^{2+}$ microdomains and the control of insulin secretion. Cell Calcium 40, 539-551, 2006
18. Spat, A. Calcium microdomains and the fine control of cell function—An introduction. Cell Calcium 40, 403-404, 2006.
19. Triantafilou & Triantafilou, 2004
20. WO 97/08202;
21. WO 05/030246
22. WO 98/21978
23. WO 00/038535

The invention claimed is:

1. A method for treatment of a condition associated with dysfunction of lipid rafts, receptors and/or caveolae in cell membranes comprising administering to a mammal in need thereof in an amount sufficient to normalize lipid raft function an antisecretory protein of SEQ ID NO:6, a fragment thereof comprising SEQ ID NO:10 and having equivalent activity, or a pharmaceutically active salt thereof; and wherein said condition is selected from the group consisting of vascular dysfunction, cardiovascular dysfunction, lung dysfunction, diabetes mellitus, hyperplasia and/or hypertrophy of cells and/or tissue, and cardiomyopathy.

2. The method of claim 1, wherein said administering is performed either as a single dose or as multiple daily applications.

3. The method of claim 1, wherein said dysfunction is selected from the group consisting of abnormal, insufficient hypo- and hyper-function.

4. A method for treatment of a condition associated with dysfunction of lipid rafts, receptors and/or caveolae in cell membranes comprising administering to a mammal in need thereof a composition comprising a pharmaceutically acceptable excipient and an antisecretory protein of SEQ ID NO:6, a fragment thereof comprising SEQ ID NO:10 and having equivalent activity, or a pharmaceutically active salt thereof, in an amount sufficient to normalize lipid raft function; and wherein said condition is selected from the group consisting of vascular dysfunction, cardiovascular dysfunction, lung dysfunction, diabetes mellitus, hyperplasia and/or hypertrophy of cells and/or tissue, and cardiomyopathy.

5. The method of claim 4, wherein said composition comprises two or more antisecretory proteins.

6. The method of claim 4, wherein said composition is formulated for intraocular, intranasal, oral, local, subcutaneous and/or systemic administration.

7. The method of claim 4, wherein said composition is formulated for administration as a spray, aerosol, inhaler or by a nebulizer.

8. The method of claim 4, wherein said composition is formulated for administration systemically to the blood at a dose of 0.1 µg to 10 mg per application and kg body weight and day, preferably 1-1000 µg per application and kg body weight and day.

9. The method of claim 4, wherein said administering is performed either as a single dose or as multiple daily applications.

10. The method of claim 4, wherein said dysfunction is selected from the group consisting of abnormal, insufficient hypo- and hyper-function.

* * * * *